United States Patent [19]

Shimizu et al.

[11] Patent Number: 4,529,530

[45] Date of Patent: Jul. 16, 1985

[54] TRIUREA GREASE COMPOSITIONS

[75] Inventors: Shirow Shimizu, Tokyo; Shuichi Takahashi, Ohmiya; Kazuo Kato, Tokyo; Koichi Takeuchi; Kozo Iwasaki, both of Mobara; Motofumi Kurahashi; Tetsuo Ichimaru, both of Tokai, all of Japan

[73] Assignees: Chuo Yuka Co., Ltd.; Mitsui Toatsu Chemicals, Inc.; Nippon Steel Corporation, all of Tokyo, Japan

[21] Appl. No.: 533,637

[22] Filed: Sep. 19, 1983

[30] Foreign Application Priority Data

Sep. 17, 1982 [JP] Japan ................... 57-160795

[51] Int. Cl.³ ................ C10M 1/20; C10M 1/32
[52] U.S. Cl. ............................ 252/51.5 A
[58] Field of Search ................... 252/51.5 A

[56] References Cited

U.S. PATENT DOCUMENTS 4,100,081 7/1978 Dreher et al. ............ 252/51.5 A
4,113,640 9/1978 Wulfers .................... 252/51.5 A

FOREIGN PATENT DOCUMENTS 53-9242 4/1978 Japan .

Primary Examiner—W. J. Shine
Attorney, Agent, or Firm—Young & Thompson

[57] ABSTRACT

Triurea grease compositions having excellent oil separation, shear stability, oxidation stability and structural stability of a thickening agent at a high temperature, which contains a triurea compound

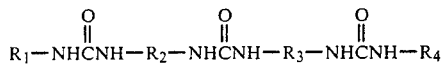

wherein $R_1$ is a monovalent aliphatic hydrocarbon radical having 12-24 carbon atoms, $R_2$ is a divalent triazine derivative radical, $R_3$ is a divalent aromatic hydrocarbon radical having 6-15 carbon atoms or the derivative radical thereof, and $R_4$ is at least one of monovalent aliphatic hydrocarbon radicals having 2-24 carbon atoms, derivative radicals thereof, monovalent aromatic hydrocarbon radicals having 6-10 carbon atoms and derivative radicals thereof, as a thickening agent in a usual lubricating base oil.

11 Claims, No Drawings

TRIUREA GREASE COMPOSITIONS

BACKGROUND OF THE INVENTION

1. Field of the Invention

This invention relates to grease compositions using novel triurea compounds which are excellent in oil separation, shear stability and oxidation stability at a high temperature and are noticeably stable in the structure of a thickening agent under severe conditions of oxidation or high temperature and the like.

2. Description of the Prior Art

Presently most broadly used greases are ones using a metal soap as a thickening agent and among them, lithium soap grease has been generally numerously used. However, greases having higher quality and longer durable life have been demanded as the lubricating conditions become more severe owing to the progress of machines and novel thickening agents having excellent thermal resistance and long durable life at a high temperature have been gradually developed.

Among the thus developed greases, urea greases are non-soap ones and contain an ashless thickening agent and therefore these greases are one of representable high temperature greases. In general, these greases are high in dropping point and are relatively stable in the structure of the thickening agent at a high temperature and contain no metallic atom which promotes the oxidation deterioration in the molecule of the thickening agent, so that the oxidation stability is generally high.

Urea compounds of the thickening agent may be produced by reacting an isocyanate with an amine in a solvent or a base oil but the urea compounds of the reaction products include a large number of urea compounds depending upon the number of urea bond

(—NHCNH—, ureilene radical), and the kind or number of radicals (hydrocarbon radicals, etc.) between the urea bonds and terminal radical of the compound, and there is a great difference in the grease property.

The most typical prior patents already reported comprise diurea grease by E. A. Swakon et al (U.S. Pat. No. 2,710,839, U.S. Pat. No. 2,710,840, U.S. Pat. No. 2,710,841) and tetraurea grease by J. L. Dreher et al (U.S. Pat. Nos. 3,242,210, 3,243,372) and the other many patents intend to develop these base patents and improve the grease properties.

However, in general the diurea greases have defects that at a high temperature the consistency softens and the oil separation is high and the tetraurea greases when exposing to a high temperature for a long period of time, readily cause the hardening of consistency. Furthermore, in the prior triurea greases (Japanese Patent No. 932,322), the consistency softens at a high temperature and in symmetrical triazine tetraurea greases (U.S. Pat. Nos. 4,026,890 and 4,113,640), the production of the thickening agent is troublesome and a long time is necessary for obtaining the final grease product.

SUMMARY OF THE INVENTION

The inventors have made studies for obviating the above described defects of the prior arts and found that triurea compounds in which a triazine radical is introduced between urea bonds, have very excellent properties as a thickening agent of a grease and that a method for producing the grease is relatively easy.

That is, asymmetrical triazine triurea greases according to the present invention have a high dropping point, are excellent in the oil separation, shear stability and oxidation stability at a high temperature and are considerably small in the variation of the grease condition after oxidation at a high temperature and when the heating and cooling are repeated, the initial consistency is substantially maintained and thus the high temperature properties are very excellent.

The greases according to the present invention can use a wide variety of lubricating oils of mineral oil and synthetic oils as the base oil and any lubricaing oils in which the viscosity is within the range of the usually used lubricating oils, can be used.

A grease composition of the present invention consists essentially of a major amount of a lubricating base oil and 2–30% by weight, preferably 4–25% by weight of a thickening agent of a triurea compound having the general formula

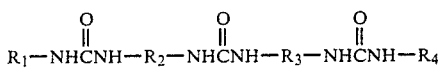

wherein $R_1$ is a monovalent aliphatic hydrocarbon radical having 12–24 carbon atoms, $R_2$ is a divalent triazine derivative radical, $R_3$ is a divalent aromatic hydrocarbon radical having 6–15 carbon atoms or the derivative radical thereof, and $R_4$ is at least one of monovalent aliphatic hydrocarbon radicals having 2–24 carbon atoms, derivative radicals thereof, monovalent aromatic hydrocarbon radicals having 6–10 carbon atoms and derivative radicals thereof.

DESCRIPTION OF THE PREFERRED EMBODIMENTS

As the monovalent aliphatic hydrocarbon radicals ($R_1$) having 12–24 carbon atoms, mention may be made of the aliphatic hydrocarbon radicals having a straight chain structure, such as dodecyl, tridecyl, tetradecyl, pentadecyl, hexadecyl, heptadecyl, octadecyl, nonadecyl, eicosyl, heneicosyl, docosyl, tricosyl, tetracosyl radicals, and hexadecyl, octadecyl and eicosyl radicals are particularly preferable.

As the divalent triazine derivative radicals ($R_2$), mention may be made of

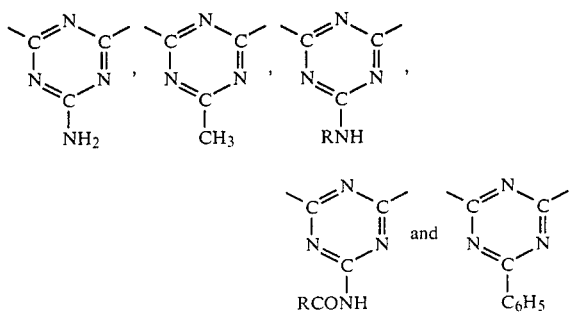

wherein R is a monovalent aliphatic hydrocarbon radical having 12–24 carbon atoms and -$C_6H_5$ is a phenyl radical, and the particularly preferable radicals are

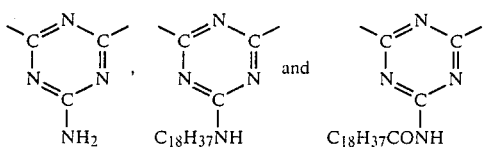

As the divalent aromatic hydrocarbon radicals (R$_3$) having 6–15 carbon atoms or the derivative radicals thereof mention may be made of

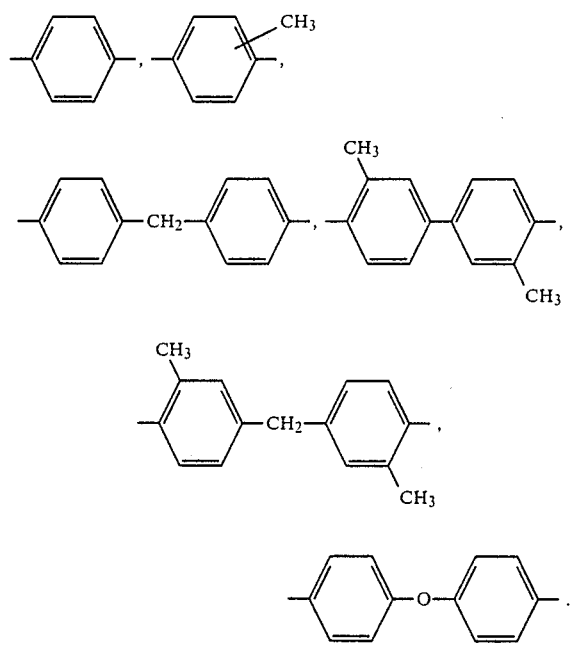

As the aliphatic hydrocarbon radicals (R$_4$) having 2–24 carbon atoms, mention may be made of saturated or unsaturated aliphatic hydrocarbon radicals such as octyl, nonyl, decyl, undecyl, dodecyl, tridecyl, tetradecyl, pentadecyl, hexadecyl, heptadecyl, octadecyl, octadecynyl, nonadecyl, eicosyl, heneicosyl, docosyl, tricosyl and tetracosyl radicals and the particularly preferable ones are hexadecyl, octadecyl and octadecynyl radicals. The derivative radicals thereof include monoethanolamine, isorpopanolamine, palmitic acid amide, stearic acid amide, etc.

As the monovalent hydrocarbon radicals (R$_4$) having 6–10 carbon atoms, mention may be made of

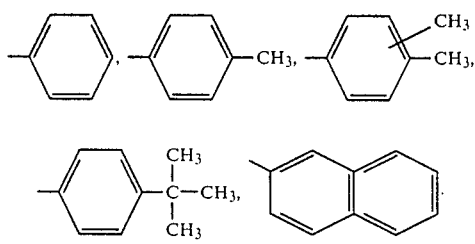

As the derivative radicals (R$_4$) thereof, mention may be made of

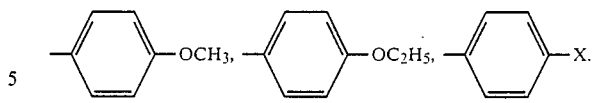

wherein X is a halogen atom such as fluorine, chlorine and bromine.

When the carbon number of R$_1$ in the above described general formula is less than 11, the oleophilic property lowers, while when said number is more than 25, the solubility lowers and the reactivity becomes poor, so that these cases are not acceptable.

R$_3$ is an aromatic hydrocarbon radical and therefore the carbon number must be 6 or more and when said number exceeds 15, both the solubility and the reactivity lower, so that such a case is not applicable.

When the carbon number of R$_4$ is less than 2, that is 1, such an amine is gaseous and the control of the reaction is difficult, while when said number is more than 25, the solubility lowers and the reactivity also lowers, so that both the cases are not acceptable. When R$_4$ is an aromatic hydrocarbon radical, the carbon number must not be less than 6 and when said number exceeds 10, both the solubility and the reactivity lower.

Then, explanation will be made with respect to the method for producing novel triurea compounds to be used as the thickening agent in the present invention. The triurea compounds are the reaction product of an N-aliphatic hydrocarbon radical substituted ureido-triazine derivative, one or more primary amines and a diisocyanate, which is shown by the following chemical reaction formula.

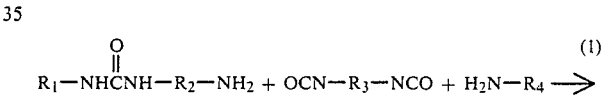

In the above described chemical reaction, the primary amine may be a combination of two or more amines as well as a single amine. When the primary amine is used in a single amine, the grease obtained from the triurea compound formed from such an amine may have an individual property of a merit and a demerit, while when two or more different amines are used in a combination, the obtained grease can develop balanced properties of these amines, so that the use of two or more amines is preferable.

The above described N-aliphatic hydrocarbon radical substituted ureido-triazine derivatives are produced by reacting a triazine derivative having two or more amino radicals with an alkyl isocyanate having 12–24 carbon atoms and this reaction is shown by the following general formula

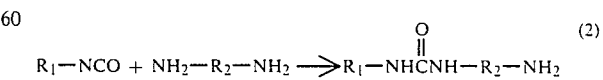

This reaction may be carried out in an equimolar ratio of an alkyl isocyanate and a triazine derivative and as an auxiliary solvent, it is preferable to use a polar organic solvent, such as dimethylformamide, dioxane, dimethylsulfoxide, etc. The reaction temperature is generally 80°-200° C., preferably 100°-160° C. and the reaction is carried out while stirring for 1-5 hours. The reaction product precipitates in the solvent, so that after completing the reaction, the reaction mass is cooled to room temperature and then filtered and the reaction product is dried to obtain N-aliphatic hydrocarbon radical substituted ureido-triazine.

The production method of a grease is as follows.

N-aliphatic hydrocarbon radical substituted ureido-triazine derivative and one or more primary amines are mixed in an equimolar ratio in a lubricating base oil and heated and dissolved and then a diisocyanate (a solution in the lubricating base oil) is gradually added in an equimolar ratio thereto while vigorously stirring. Then, the reaction product is heated to a given temperature (150°-220° C.) while thoroughly stirring, after which the reaction mixture is cooled to room temperature and milled to obtain the product.

In the method of the above mentioned U.S. Pat. Nos. 4,026,890 and 4,113,640, wherein this reaction is not performed in a lubricating base oil, but in a volatilizing organic solvent, troublesome operations such as removal of a solvent, grinding of the reaction product and incorporating into the lubricating base oil, are necessary and this method has a drawback that a long time is required for the preparation. Accordingly, the present invention wherein the preparation is performed in the lubricating base oil is more advantageous than these prior arts.

The thus prepared grease compositions may be added with additives such as extreme pressure additives, oxidation inhibitors, oil improvers, anticorrosion additives, viscosity index improvers and the like without damaging the properties in order to improve the grease performances.

The content of the triurea compounds is preferred to be 2-30% by weight, preferably 4-25% by weight. When the amount of the triurea compounds are less than 2% by weight, the thickening activity is lower, while when said amount exceeds 30% by weight, the grease becomes too hard and a satisfactory lubricating effect cannot be attained and such an amount is disadvantageous in view of economy.

The thus prepared greases show superior properties to the other prior commercially available greases as explained in the following examples.

The following examples are given for the purpose of illustration of this invention and are not intended as limitations thereof.

EXAMPLES 1-30

87.5 g of 2-octadecylureido-4-octadecylamino-1,3,5-triazine, 35.0 of octadecylamine and 445.0 g of paraffin refined mineral oil (Kinematic viscosity @100° C., 10.48 cst, viscosity index 99) were charged in a reaction vessel and uniformly mixed and dissolved by heating up to about 80° C. Separately, 32.5 g of an equimolar ratio of diphenylmethane-4,4'-diisocyanate has been uniformly dissolved in 400 g of the same paraffin refined mineral oil as described above by heating at about 80° C. and this solution was gradually added to the above described mixture while vigorously stirring. The resulting mixture subsequently was heated up to 185° C. while vigorously stirring. Then, the reaction mixture was cooled to room temperature and roll-finished to obtain a smooth grease.

The properties of the obtained greases are shown in the following Table 2.

In Examples 2-30, the grease compositions were prepared in the same manner as described in Example 1 except for varying the used starting material and the highest treating temperatures for the preparation as shown in the following Table 1.

TABLE 1

| Example | Triazine derivatives Kind | g | Primary amines Kind | g | Diisocyanates Kind | g | Base oils Kind | g | Highest treating temperature (°C.) |
|---|---|---|---|---|---|---|---|---|---|
| 2 | DSM* | 105.2 | Octadecylamine p-toluidine | 20.2 8.0 | MDI**** | 37.5 | Paraffin mineral oil (Kinematic viscosity @ 100° C., 10.48 cst) | 829.1 | 185 |
| 3 | MCG** | 63.2 | Octadecylamine Stearic acid amide | 20.2 21.2 | MDI | 37.5 | Paraffin mineral oil (Kinematic viscosity @ 100° C., 13.59 cst) | 857.9 | 160 |
| 4 | DSM | 98.1 | Hexadecylamine p-anisidine | 16.9 8.6 | MDI | 35.0 | Pentaerythritol tetracaprate (Kinematic viscosity @ 98.9° C., 7.34 cst) | 841.4 | 200 |
| 5 | ATT*** | 101.0 | Oleylamine p-toluidine | 20.0 8.0 | TODI***** | 39.6 | Methylphenyl polysiloxane (Kinematic viscosity @ 25° C., 400 cst) | 831.4 | 220 |
| 6 | MCG | 63.2 | Octadecylamine p-chloroaniline | 20.2 9.5 | TODI | 39.6 | Paraffin mineral oil (Kinematic viscosity @ 100° C., 13.59 cst) | 867.5 | 200 |
| 7 | MCG | 58.2 | Octadecylamine | 37.2 | MDI | 34.6 | Paraffin mineral oil (Kinematic viscosity @ 100° C., 13.59 cst) | 870.0 | 170 |
| 8 | DSM | 80.4 | Octadecylamine | 30.9 | MDI | 28.7 | Paraffin mineral oil (Kinematic viscosity @ 100° C., 13.59 cst) | 860.0 | 170 |
| 9 | DSM | 99.4 | p-toluidine | 15.2 | MDI | 35.4 | Paraffin mineral oil (Kinematic viscosity @ 100° C., 32.89 cst) | 850.0 | 170 |
| 10 | ATT | 95.4 | Hexadecylamine | 34.2 | MDI | 35.4 | Paraffin mineral oil (Kinematic viscosity @ 100° C., 32.89 cst) | 835.0 | 185 |
| 11 | MCG | 75.0 | Stearic acid amide | 50.4 | MDI | 44.6 | Paraffin mineral oil (Kinematic viscosity @ 100° C.. 32.89 cst) | 830.0 | 200 |

TABLE 1-continued

| Example | Triazine derivatives Kind | g | Primary amines Kind | g | Diisocyanates Kind | g | Base oils Kind | g | Highest treating temperature (°C.) |
|---|---|---|---|---|---|---|---|---|---|
| 12 | MCG | 79.5 | p-anisidine | 23.2 | MDI | 47.2 | Paraffin mineral oil (Kinematic viscosity @ 100° C., 32.89 cst) | 850.1 | 170 |
| 13 | MCG | 61.8 | Octadecylamine | 39.5 | TODI | 38.7 | Pentaerythritol tetracaprate (Kinematic viscosity @ 98.9° C., 7.34 cst) | 860.0 | 200 |
| 14 | ATT | 84.9 | Aniline | 11.7 | TODI | 33.3 | Pentaerythritol tetracaprate (Kinematic viscosity @ 98.9° C., 7.34 cst) | 870.1 | 200 |
| 15 | ATT | 70.0 | Octadecylamine Aniline | 19.6 2.9 | TODI | 27.5 | Paraffin mineral oil (Kinematic viscosity @ 100° C., 10.48 cst) | 880.0 | 160 |
| 16 | DSM | 95.3 | Oleylamine p-chloroaniline | 21.8 7.0 | TODI | 35.9 | Paraffin mineral oil (Kinematic viscosity @ 100° C., 13.59 cst) | 840.0 | 185 |
| 17 | DSM | 88.7 | Hexadecylamine p-phenetydine | 24.4 3.5 | TODI | 33.4 | Methylphenyl polysiloxane (Kinematic viscosity @ 25° C., 400 cst) | 850.0 | 220 |
| 18 | DSM | 106.3 | Octadecylamine Monoethanolamine | 12.2 6.5 | TODI | 40.0 | Paraffin mineral oil (Kinematic viscosity @ 100° C., 32.89 cst) | 835.0 | 170 |
| 19 | ATT | 68.5 | Octadecylamine p-phenetydine | 21.9 2.8 | TODI | 26.9 | Paraffin mineral oil (Kinematic viscosity @ 100° C., 32.89 cst) | 879.9 | 200 |
| 20 | MCG | 77.1 | Palmitic acid amide p-anisidine | 32.7 6.7 | TODI | 48.4 | Paraffin mineral oil (Kinematic viscosity @ 100° C., 13.59 cst) | 835.1 | 185 |
| 21 | MCG | 58.3 | Octadecylamine p-anisidine | 18.6 8.5 | MDI | 34.6 | Methylphenyl polysiloxane (Kinematic viscosity @ 25° C., 400 cst) | 880.0 | 200 |
| 22 | ATT | 98.8 | Stearic acid amide p-anisidine | 29.1 5.4 | MDI | 36.7 | Paraffin mineral oil (Kinematic viscosity @ 100° C., 10.48 cst) | 830.0 | 185 |
| 23 | ATT | 91.2 | Octadecylamine Palmitic acid amide | 7.3 27.6 | MDI | 33.9 | Paraffin mineral oil (Kinematic viscosity @ 100° C., 32.89 cst) | 840.0 | 185 |
| 24 | DSM | 96.8 | Octadecylamine Stearic acid amide | 7.4 31.2 | MDI | 34.5 | Paraffin mineral oil (Kinematic viscosity @ 100° C., 32.89 cst) | 830.1 | 170 |
| 25 | DSM | 78.4 | Hexadecylamine Aniline | 13.5 5.2 | MDI | 28.0 | Paraffin mineral oil (Kinematic viscosity @ 100° C., 32.89 cst) | 874.9 | 170 |
| 26 | DSM | 77.7 | Octadecylamine Palmitic acid amide Aniline | 14.9 7.1 2.6 | MDI | 27.7 | Paraffin mineral oil (Kinematic viscosity @ 100° C., 32.89 cst) | 870.0 | 170 |
| 27 | MCG | 60.3 | Octadecylamine Stearic acid amide p-anisidine | 19.3 10.1 4.4 | MDI | 35.8 | Paraffin mineral oil (Kinematic viscosity @ 100° C., 32.89 cst) | 870.1 | 180 |
| 28 | MCG | 75.8 | Octadecylamine Isopropanolamine p-toluidine Aniline | 19.4 2.7 3.9 3.3 | MDI | 45.0 | Paraffin mineral oil (Kinematic viscosity @ 100° C., 32.89 cst) | 849.9 | 170 |
| 29 | MCG | 75.1 | Hexadecylamine Stearic acid amide p-phenetidine p-toluidine | 25.8 10.1 2.5 1.9 | MDI | 44.6 | Paraffin mineral oil (Kinematic viscosity @ 100° C., 32.89 cst) | 840.0 | 185 |
| 30 | ATT | 84.3 | Octadecylamine Stearic acid amide Monoethanolamine p-chloroaniline | 13.5 7.1 2.3 1.6 | MDI | 31.3 | Paraffin mineral oil (Kinematic viscosity @ 100° C., 32.89 cst) | 859.9 | 200 |

Note:
*DSM: 2-octadecylureido-4-octadecanolylamino-1,3,5-triazine
**MCG: 2-octadecylureido-4,6-diamino-1,3,5-triazine
***ATT: 2-octadecylureido-4-octadecylamino-1,3,5-triazine
****MDI: diphenylmethane-4,4'-diisocyanate
*****TODI: 3,3'-bitolylene-4,4'-diisocyanate The properties of the greases obtained in the above described examples are shown in the following Table 2. The same test was performed with respect to the commercially available urea greases (Comparative Example 1: a commercially available diurea grease, Comparative Example 2: a commercially available tetraurea grease, Comparative Example 3: a commercially available triurea grease) and the properties of these greases are shown in the following Table 2. Test methods:
1. Worked penetration: Following to ASTM D217
2. Dropping point: Following to ASTM D566

3. Oil separation: Following to FTM 791 B-321.2
4. Oxidation stability:
   (1) Following to ASTM D942, the test was performed at 150° C. for 200 hours.
   (2) The worked penetration of the grease after the test was measured by means of ¼-scale cone following to ASTM D1403, reference 1.
   (3) Dropping point of the grease after the test was followed to ASTM D566.
5. Heating-cooling cycle test:

A sample was charged and filled in a pot for measuring ½ scale cone penetration and heating in an air bath kept at a constant temperature of 150° C. and 180° C. for 20 hours and then taken out and cooled in air for 4 hours.

Unworked penetration was measured by means of ½ scale cone following to ASTM D1403 reference 1. This operation was conducted in 4 cycles.

6. Roll stability:
This test was conducted following to ASTM D1831 at 100° C. for 24 hours and at 150° C. for 24 hours.

TABLE 2

| Test items | | Example 1 | Example 2 | Example 3 | Example 4 | Example 5 | Example 6 | Example 7 |
|---|---|---|---|---|---|---|---|---|
| Worked penetration | | 274 | 285 | 283 | 279 | 277 | 280 | 285 |
| Dropping point (°C.) | | 258 | 275 | 274 | 268 | 269 | 265 | 257 |
| Oil separation | | | | | | | | |
| 100° C., 24 hr (%) | | 1.4 | 0.9 | 0.6 | 1.0 | 0.8 | 1.2 | 0.8 |
| 150° C., 24 hr (%) | | 1.0 | 0.7 | 1.3 | 1.2 | 0.7 | 1.0 | 0.4 |
| Oxidation stability 150° C., 200 hr (kgf/cm²) | | 2.00 | 2.25 | 2.15 | 2.15 | 2.05 | 2.20 | 1.95 |
| Form of grease after test | | grease-like | grease-like | grease-like | grease-like | grease-like | grease-like | grease-like |
| Worked penetration of grease after test | | 276 | 290 | 294 | 291 | 300 | 294 | 298 |
| Dropping point of grease after test (°C.) | | 249 | 268 | 273 | 265 | 260 | 257 | 252 |
| Heating-cooling cycle test | | | | | | | | |
| Unworked penetration after cycle of heating at 150° C. for 20 hours and cooling by leaving in air for 4 hours | 1 cycle | 239 | 258 | 246 | 251 | 236 | 254 | 251 |
| | 2 cycle | 240 | 253 | 249 | 244 | 240 | 246 | 250 |
| | 3 cycle | 235 | 259 | 251 | 238 | 234 | 241 | 246 |
| | 4 cycle | 235 | 242 | 260 | 239 | 231 | 239 | 246 |
| Unworked penetration after cycle of heating at 180° C. for 20 hours and cooling by leaving in air for 4 hours | 1 cycle | 245 | 263 | 251 | 250 | 253 | 252 | 255 |
| | 2 cycle | 263 | 269 | 272 | 263 | 250 | 260 | 261 |
| | 3 cycle | 275 | 271 | 289 | 274 | 259 | 273 | 270 |
| | 4 cycle | 280 | 285 | 294 | 289 | 267 | 287 | 284 |
| Roll stability | | | | | | | | |
| 100° C., 24 hr | | 290 | 298 | 291 | 296 | 291 | 290 | 315 |
| 150° C., 24 hr | | 286 | 297 | 293 | 300 | 291 | 302 | 310 |

| Test items | | Example 8 | Example 9 | Example 10 | Example 11 | Example 12 | Example 13 | Example 14 |
|---|---|---|---|---|---|---|---|---|
| Worked penetration | | 269 | 280 | 281 | 274 | 290 | 284 | 278 |
| Dropping point (°C.) | | 263 | 262 | 270 | 268 | 263 | 274 | 280 |
| Oil separation | | | | | | | | |
| 100° C., 24 hr (%) | | 1.2 | 1.5 | 0.7 | 1.1 | 0.9 | 0.9 | 1.4 |
| 150° C., 24 hr (%) | | 0.8 | 0.9 | 0.4 | 0.6 | 0.6 | 0.3 | 1.0 |
| Oxidation stability 150° C., 200 hr (kgf/cm²) | | 2.10 | 2.35 | 2.25 | 2.25 | 2.20 | 2.00 | 2.20 |
| Form of grease after test | | grease-like | grease-like | grease-like | grease-like | grease-like | grease-like | grease-like |
| Worked penetration of grease after test | | 276 | 302 | 300 | 285 | 292 | 284 | 287 |
| Dropping point of grease after test (°C.) | | 251 | 253 | 268 | 261 | 259 | 268 | 273 |
| Heating-cooling cycle test | | | | | | | | |
| Unworked penetration after cycle of heating at 150° C. for 20 hours and cooling by leaving in air for 4 hours | 1 cycle | 239 | 254 | 245 | 246 | 268 | 247 | 247 |
| | 2 cycle | 242 | 254 | 239 | 245 | 268 | 245 | 240 |
| | 3 cycle | 238 | 260 | 241 | 238 | 274 | 244 | 241 |
| | 4 cycle | 233 | 261 | 236 | 237 | 270 | 239 | 235 |
| Unworked penetration after cycle of heating at 180° C. for 20 hours and cooling by leaving in air for 4 hours | 1 cycle | 242 | 263 | 248 | 252 | 265 | 253 | 262 |
| | 2 cycle | 260 | 272 | 258 | 254 | 274 | 258 | 272 |
| | 3 cycle | 273 | 280 | 264 | 261 | 286 | 271 | 279 |
| | 4 cycle | 282 | 291 | 277 | 272 | 299 | 283 | 292 |
| Roll stability | | | | | | | | |
| 100° C., 24 hr | | 297 | 287 | 299 | 280 | 332 | 298 | 298 |
| 150° C., 24 hr | | 301 | 294 | 303 | 286 | 328 | 304 | 308 |

| Test items | Example 15 | Example 16 | Example 17 | Example 18 | Example 19 | Example 20 | Example 21 |
|---|---|---|---|---|---|---|---|
| Worked penetration | 283 | 280 | 276 | 288 | 283 | 274 | 270 |
| Dropping point (°C.) | 271 | 261 | 259 | 276 | 269 | 260 | 266 |
| Oil separation | | | | | | | |
| 100° C., 24 hr (%) | 0.9 | 1.3 | 1.3 | 0.6 | 0.8 | 1.2 | 0.8 |
| 150° C., 24 hr (%) | 1.0 | 1.1 | 0.8 | 0.5 | 1.2 | 1.0 | 0.6 |
| Oxidation stability 150° C., 200 hr (kgf/cm²) | 2.05 | 2.15 | 2.15 | 2.25 | 2.05 | 2.20 | 2.15 |
| Form of grease after test | grease-like | grease-like | grease-like | grease-like | grease-like | grease-like | grease-like |
| Worked penetration of grease after test | 289 | 301 | 284 | 300 | 282 | 291 | 293 |
| Dropping point of grease after test (°C.) | 263 | 251 | 250 | 274 | 259 | 270 | 267 |

TABLE 2-continued

| Heating-cooling cycle test | | | | | | | | |
|---|---|---|---|---|---|---|---|---|
| Unworked penetration after cycle | 1 cycle | 267 | 242 | 251 | 259 | 253 | 234 | 237 |
| of heating at 150° C., for 20 hours | 2 cycle | 262 | 248 | 247 | 261 | 255 | 230 | 241 |
| and cooling by leaving in air | 3 cycle | 255 | 242 | 242 | 260 | 254 | 229 | 245 |
| for 4 hours | 4 cycle | 248 | 239 | 236 | 253 | 246 | 226 | 256 |
| Unworked penetration after cycle | 1 cycle | 269 | 249 | 260 | 266 | 255 | 240 | 258 |
| of heating at 180° C. for 20 hours | 2 cycle | 272 | 258 | 264 | 274 | 261 | 257 | 263 |
| and cooling by leaving in air | 3 cycle | 278 | 271 | 270 | 283 | 269 | 255 | 271 |
| for 4 hours | 4 cycle | 282 | 284 | 274 | 295 | 280 | 274 | 290 |
| Roll stability | | | | | | | | |
| 100° C., 24 hr | | 313 | 297 | 306 | 318 | 312 | 294 | 309 |
| 150° C., 24 hr | | 315 | 295 | 315 | 325 | 317 | 298 | 304 |

| Test items | | Example 22 | Example 23 | Example 24 | Example 25 | Example 26 | Example 27 | Example 28 |
|---|---|---|---|---|---|---|---|---|
| Worked penetration | | 277 | 281 | 279 | 285 | 280 | 273 | 291 |
| Dropping point (°C.) | | 272 | 275 | 264 | 272 | 268 | 268 | 278 |
| Oil separation | | | | | | | | |
| 100° C., 24 hr (%) | | 1.1 | 0.5 | 1.6 | 1.0 | 1.5 | 0.8 | 0.8 |
| 150° C., 24 hr (%) | | 1.1 | 0.9 | 0.7 | 0.5 | 1.2 | 1.4 | 0.6 |
| Oxidation stability 150° C., 200 hr (kgf/cm$^2$) | | 2.30 | 2.25 | 2.05 | 2.20 | 2.15 | 2.30 | 2.00 |
| Form of grease after test | | grease-like | grease-like | grease-like | grease-like | grease-like | grease-like | grease-like |
| Worked penetration of grease after test | | 293 | 284 | 294 | 293 | 297 | 285 | 295 |
| Dropping point of grease after test (°C.) | | 265 | 266 | 253 | 266 | 260 | 254 | 270 |
| Heating-cooling cycle test | | | | | | | | |
| Unworked penetration after cycle | 1 cycle | 240 | 257 | 252 | 250 | 242 | 240 | 269 |
| of heating at 150° C. for 20 hours | 2 cycle | 241 | 253 | 248 | 242 | 238 | 241 | 264 |
| and cooling by leaving in air | 3 cycle | 247 | 246 | 249 | 240 | 235 | 248 | 257 |
| for 4 hours | 4 cycle | 250 | 233 | 245 | 233 | 230 | 245 | 250 |
| Unworked penetration after cycle | 1 cycle | 251 | 267 | 264 | 259 | 252 | 253 | 274 |
| of heating at 180° C. for 20 hours | 2 cycle | 261 | 279 | 265 | 268 | 260 | 264 | 284 |
| and cooling by leaving in air | 3 cycle | 273 | 287 | 269 | 278 | 271 | 278 | 291 |
| for 4 hours | 4 cycle | 288 | 302 | 268 | 291 | 289 | 299 | 298 |
| Roll stability | | | | | | | | |
| 100° C., 24 hr | | 313 | 287 | 285 | 316 | 288 | 280 | 302 |
| 150° C., 24 hr | | 317 | 289 | 285 | 320 | 291 | 279 | 297 |

| Test items | | Example 29 | Example 30 | Comparative Example 1 | Comparative Example 2 | Comparative Example 3 |
|---|---|---|---|---|---|---|
| Worked penetration | | 285 | 278 | 283 | 271 | 290 |
| Dropping point (°C.) | | 280 | 269 | 265 | 262 | 271 |
| Oil separation | | | | | | |
| 100° C., 24 hr (%) | | 1.2 | 1.5 | 1.4 | 4.6 | 4.4 |
| 150° C., 24 hr (%) | | 1.3 | 0.7 | 1.9 | 3.9 | 3.6 |
| Oxidation stability 150° C., 200 hr (kgf/cm$^2$) | | 1.95 | 2.05 | 2.40 | 4.05 | 3.15 |
| Form of grease after test | | grease-like | grease-like | liquid | liquid | liquid |
| Worked penetration of grease after test | | 292 | 284 | — | — | — |
| Dropping point of grease after test (°C.) | | 274 | 258 | — | — | — |
| Heating-cooling cycle test | | | | | | |
| Unworked penetration after cycle | 1 cycle | 248 | 250 | 121 | 125 | more than 400 |
| of heating at 150° C. for 20 hours | 2 cycle | 247 | 245 | 103 | 123 | more than 400 |
| and cooling by leaving in air | 3 cycle | 242 | 243 | 104 | 120 | more than 400 |
| for 4 hours | 4 cycle | 239 | 240 | 98 | 121 | more than 400 |
| Unworked penetration after cycle | 1 cycle | 259 | 260 | 135 | 142 | more than 400 |
| of heating at 180° C. for 20 hours | 2 cycle | 268 | 268 | 127 | 121 | more than 400 |
| and cooling by leaving in air | 3 cycle | 277 | 271 | 107 | 110 | more than 400 |
| for 4 hours | 4 cycle | 286 | 283 | 92 | 113 | more than 400 |
| Roll stability | | | | | | |
| 100° C., 24 hr | | 299 | 290 | 230 | 380 | 372 |
| 150° C., 24 hr | | 294 | 296 | 251 | more than 400 | more than 400 |

When Examples 1-30 are compared with the commercially available prior urea greases of Comparative Examples 1-3, both the oil separation and the roll stability at 100° C. and 150° C. and the oxidation stability at 150° C. in the examples are superior to those of the comparative examples. Concerning the grease form after the test of the oxidation stability, any three comparative examples of the commercially available urea greases are liquid and the grease structure is broken, while all the greases of the present invention maintain the grease form and can expect the lubricating activity at a high temperature for a long period of time.

In the heating-cooling cycle test at 150° C. and 180° C., the consistency of the commercially available urea greases show the noticeable hardening and softening, while the greases of the present invention keep the original consistency and show that the structural stability of the thickening agent of the greases according to the present invention is very high.

Thus, it can be said that the triurea greases according to the present invention are far more excellent in the high temperature properties than the prior urea greases.

What is claimed is:

1. Triurea grease compositions consisting essentially of a major amount of a lubricating base oil and 2–30% by weight of a thickening agent of a triurea compound having the general formula

wherein $R_1$ is a monovalent aliphatic hydrocarbon radical having 12–24 carbon atoms, $R_2$ is a divalent triazine derivative radical, $R_3$ is a divalent aromatic hydrocarbon radical having 6–15 carbon atoms or the derivative radical thereof, and $R_4$ is at least one of monovalent aliphatic hydrocarbon radicals having 2–24 carbon atoms, derivative radicals thereof, monovalent aromatic hydrocarbon radicals having 6–10 carbon atoms and derivative radicals thereof.

2. The composition as claimed in claim 1, wherein an amount of the triurea compound is 4–25% by weight.

3. The composition as claimed in claim 1, wherein $R_1$ is selected from the group consisting of dodecyl, tridecyl, tetradecyl, pentadecyl, hexadecyl, heptadecyl, octadecyl, nonadecyl, eicosyl, heneicosyl, docosyl, tricosyl and tetracosyl radicals, which have a straight-chain structure.

4. The composition as claimed in claim 3, wherein $R_1$ is selected from the group consisting of hexadecyl, octadecyl and eicosyl radicals.

5. The composition as claimed in claim 1, wherein $R_2$ is selected from the group consisting of

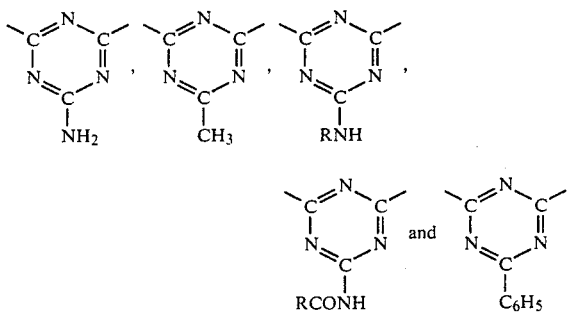

wherein R is a monovalent aliphatic hydrocarbon radical having 12–24 carbon atoms.

6. The composition as claimed in claim 5, wherein $R_2$ is selected from the group consisting of

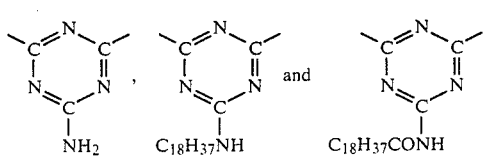

7. The composition as claimed in claim 1, wherein $R_3$ is selected from the group consisting of

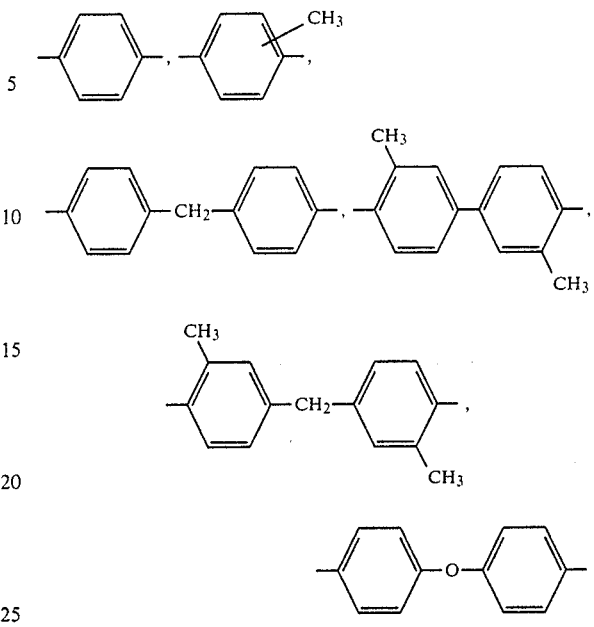

8. The composition as claimed in claim 1, wherein $R_4$ is an aliphatic hydrocarbon radical selected from the group consisting of octyl, nonyl, decyl, undecyl, dodecyl, tridecyl, tetradecyl, pentadecyl, hexadecyl, heptadecyl, octadecyl, octadecynyl, nonadecyl, eicosyl, heneicosyl, docosyl, tricosyl and tetracosyl radicals.

9. The composition as claimed in claim 8, wherein $R_4$ is selected from the group consisting of hexadecyl, octadecyl and octadecynyl radicals.

10. The composition as claimed in claim 1, wherein $R_4$ is an aliphatic hydrocarbon derivative radical selected from the group consisting of monoethanolamine, isopropanolamine, palmitic acid amide and stearic acid amide.

11. The composition as claimed in claim 1, wherein $R_4$ is an aromatic hydrocarbon radical or a derivative radical thereof selected from the group consisting of

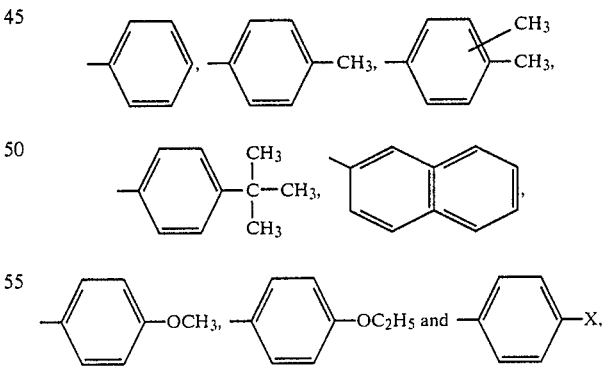

wherein X is a halogen atom of fluorine, chlorine or bromine.

* * * * *